United States Patent [19]
Bose

[11] 3,943,123
[45] Mar. 9, 1976

[54] NOVEL BETA-LACTAMS AND NOVEL PROCESS

[75] Inventor: Ajay K. Bose, Mountain Lakes, N.J.

[73] Assignee: Koninklijke Nederlandsche Gist-En Spiritusfabriek N.V., Delft, Netherlands

[22] Filed: Feb. 14, 1974

[21] Appl. No.: 442,438

Related U.S. Application Data

[63] Continuation of Ser. No. 139,231, April 30, 1971, abandoned.

[52] U.S. Cl. ...... 260/239 A; 260/295 L; 260/326 N; 260/347.3; 260/566 R; 424/244
[51] Int. Cl.$^1$ ......... C07D 205/08; C07D 405/04; C07D 403/04
[58] Field of Search......... 260/239 A, 326 N, 347.3, 260/239 A

[56] References Cited
OTHER PUBLICATIONS
Bose et al., Chem. Abs. 79, 126176m, (1973).
Bose et al., Chem. Abs. 79, 31750e, (1973).

*Primary Examiner*—Richard J. Gallagher
*Assistant Examiner*—Marh L. Berch
*Attorney, Agent, or Firm*—Hammond & Littell

[57] ABSTRACT

Novel β-lactams containing a free carboxylic group of the formula:

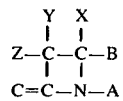

wherein A and B are each selected from the group consisting of alkyl, including but not limited to branched alkyl, aryl, aralkyl and monocyclic heterocyclic groups at least one of A and B having a free carboxylic group. Further potential substituents of A and B are members of the group consisting of hydroxy, alkoxy, halogen, nitro, $-NH_2$, monoalkylamino and dialkylamino groups, X is selected from the group consisting of hydrogen, alkyl, aryl and monocyclic heterocyclic, Y is selected from the group consisting of hydrogen, alkyl and aryl, and Z is selected from the group consisting of alkyl, alkoxy, aryloxy, aralkoxy, alkylthio, arylthio, aralkylthio, —CN, —COO-alkyl and $-N_3$, useful as antibiotics and for the preparation of polymers and β-amino acids, novel process for their preparation and novel imines used as starting materials for the said β-lactams.

8 Claims, No Drawings

NOVEL BETA-LACTAMS AND NOVEL PROCESS

This is a continuation of application Ser. No. 139,231 now abandoned filed Apr. 30, 1971.

STATE OF THE ART

There has been a great deal of interest in the last few years in processes for the production of various monocyclic β-lactams in the hope that they would be useful intermediates for the preparation of novel bicyclic compounds having good anti-bacterial activity or which might have antibacterial activity themselves. Various groups have attempted to produce monocyclic β-lactams from penicillins.

In pencillins and cephalosporins of the formula

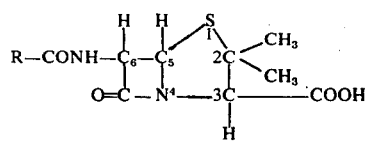

and

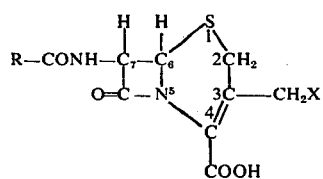

wherein R is the remainder of an acyl radical and X is hydrogen, OH, or acetoxy, a free carboxy group at the 3-position of the penicillins or at the 4-position of the cephalosporins is apparently highly desirable for antibiotic activity, normal saponification of the corresponding methyl or higher esters is unsuitable since the β-lactam ring is in most cases cleaved under these conditions.

Circuitous methods have been used to obtain free acid β-lactams in which a special ester, such as the 2,2,2-trichloroethyl ester or a benzyl ester is used during the synthesis and these esters are cleaved by special reagents such as zinc and acetic acid under mild conditions for the former and hydrogenation in presence of a catalyst such as palladized carbon in the latter.

Several groups have produced monocyclic β-lactams from natural penicillins as intermediates for the preparation of bicyclic β-lactams analogous to penicillins and cephalosporins. Sheehan et al [J. A. C. S., Vol 87, (1965), P. 5468–5469,] have described a multiple-step process for the production of monocyclic β-lactam from a 6-"blocked" aminopenicillanic acid which leads to a product of the formula A which contains a free carboxylic group,

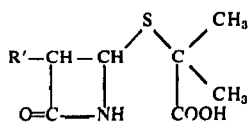 A wherein R' is the blocking group such as a phthalimido group.

A recent method of producing substituted monocyclic β-lactams from penicillins described by R. D. C. Cooper et al [Abstracts of Am. Chem. Soc. National Meeting, Sept. 1970, p. Med. 12] cleaves the thiazolidine ring of the sulfoxide of a penicillin ester to give an intermediate β-lactam ester of type

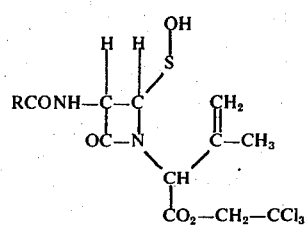 B which has the potential for providing the corresponding free acid by the action of zinc and acid.

The direct synthesis of monocyclic β-lactams can be achieved by various methods but to obtain a β-lactam with a free carboxyl group, first a β-lactam ester [for example, the special esters described above ] has to be prepared and then the ester group has to be cleaved by special techniques to leave the β-lactam group intact.

OBJECTS OF THE INVENTION

It is an object of the invention to provide a novel economical process for the production of β-lactams of formula I having free carboxylic groups.

It is another object of the invention to provide novel substituted β-lactams of formula I having free carboxylic groups.

It is an additional object of the invention to provide a novel process for the production of imines substituted with a free carboxylic group and to provide novel imines.

These and other objects and advantages of the invention will become obvious from the following detailed description.

The novel β-lactams of the invention having a free carboxylic group have the formula:

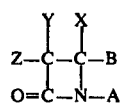 I wherein A and B are each selected from the group consisting of alkyl, including but not limited to branched alkyl, aryl, aralkyl and monocyclic heterocyclic groups, at least one of A and B having a free carboxylic group. Further potential substituents of A and B are members of the group consisting of hydroxy, alkoxy, halogen, nitro, $NH_2$, monoalkylamino and dialkylamino groups, X is selected from the group consisting of a hydrogen atom and alkyl, aryl and monocyclic heterocyclic groups, Y is selected from the group consisting of a hydrogen atom and alkyl and aryl groups, and Z is selected from the group consisting of alkyl, alkoxy, aryloxy, aralkoxy, alkylthio, arylthio, aralkylthio, —CN, —COOAlkyl and —$N_3$. In the preferred compounds X and Y are both hydrogen. The β-lactams can be in cis and/or trans form.

Examples of suitable substituents for Y are hydrogen or lower alkyl such as methyl, ethyl, isopropyl, butyl or monocyclic aryl such as phenyl, halophenyl, lower alkyl and alkoxyphenyl and nitrophenyl. Examples of suitable substituents for Z are lower alkoxy such as methoxy and ethoxy, phenoxy, $N_3$, lower alkyl thio, monocyclic arylthio, and phthalimido.

At least one of A and B have to contain a free carboxylic group and can be alkyl and aryl of 1 to 18 carbon atoms, preferably 1 to 7 carbon atoms, such as methyl, propyl, isobutyl, α-carboxy-β-methylpropyl, 2-ethylhexyl, dodecyl; benzyl, methoxybenzyl, 3.4-dimethoxybenzyl; monocyclic aryl, such as phenyl, carboxyphenyl, such as 4-carboxyphenyl, 4-carboalkoxyphenyl, lower alkoxyphenyl, nitrophenyl, dialkylaminophenyl, hydroxyphenyl; monocyclic heterocyclic groups such as furyl, tetrahydrofuryl and pyridyl, all of which may be substituted with a carboxy group. X may be hydrogen; or alkyl and aryl groups of 1 to 18 carbon atoms amongst which especially lower alkyl groups and monocyclic aryl groups; and monocyclic heterocyclic groups such as α-furyl and α-tetrahydrofuryl groups.

The novel β-lactams of formula I can be prepared by reacting an imine wherein free hydroxy and carboxylic groups are silylated of the formula:

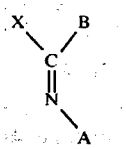

II wherein A, B and X are as hereinbefore defined with an active acylating compound of the formula:

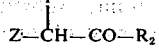

III wherein Y and Z are as hereinbefore defined and $R_2$ is selected from the group consisting of halogen, especially chlorine, $OR_3$ and $O — CO — R_4$; $R_3$ is selected from the group consisting of alkyl, aralkyl and aryl and $R_4$ is the residue of an organic carboxylic acid, to form a compound of formula I after in situ mild hydrolysis of any silyl groups present.

The reaction of the imine with the active acylating components is preferably effected in a non-hydroxylic organic solvent at temperatures from 0° to 100° C, preferably about room temperature, in the presence of a tertiary base such as triethylamine or pyridine. The inert organic solvent may be a halogenated solvent such as methylene chloride, chloroform, carbon tetrachloride, benzene, dimethylformamide and diethyl ether. The preferred active acylating components are the acid halides such as the chlorides or bromides, although other derivatives such as the acid anhydride or mixed acid anhydride or active esters can also be used. To form mixed anhydrides, the lower alkanoic acids are preferably employed.

Carboxylic and hydroxy groups present in the imino compound can be protected with a silyl ester group, which can be prepared by reacting under anhydrous conditions, a silyl compound of the formula:

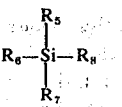

IV wherein $R_5$ is selected from the group consisting of halogen atoms, a $CH_2—CO—NH_2$ group and

$R_6$, $R_7$ and $R_8$ are each selected from the group consisting of hydrogen, halogen, alkyl and haloalkyl of 1 to 10 carbon atoms and aryl, preferably monocyclic aryl, at least one of $R_6$, $R_7$ and $R_8$ being other than hydrogen and halogen, $R_9$ is selected from the group consisting of hydrogen and alkyl of 1 to 7 carbon atoms and $R_{10}$ is selected from the group consisting of hydrogen, alkyl of 1 to 7 carbon atoms and $—SiR_6R_7R_8$ in the presence of an acid binding agent. Examples of suitable acid binding agents are tertiary amines such as triethylamine, dimethylaniline, quinoline, lutidine and pyridine.

Examples of suitable silyl compounds are trimethyl chlorosilane, hexamethyl disilazane, triethyl chlorosilane, methyl trichlorosilane, dimethyl dichlorosilane, triethylbromosilane, tri-n-propyl chlorosilane, bromomethyl dimethyl chlorosilane, tri-n-butyl chlorosilane, methyl diethyl chlorosilane, dimethyl ethyl chlorosilane, phenyl dimethyl bromosilane, benzyl methyl ethyl chlorosilane, phenyl ethyl methyl chlorosilane, triphenylchlorosilane, triphenyl fluorosilane, tri-o-tolyl chlorosilane, tri-p-dimethylaminophenyl chlorosilane, N-ethyl triethylsilylamine, hexaethyl disilazane, triphenyl silylamine, tri-n-propyl silylamine, tetraethyl dimethyl disilazane, tetramethyl diethyl disilazane, tetramethyl diphenyl disilazane, hexaphenyl disilazane, hexa-p-tolyl disilazane, etc. The same effect is produced by hexa-p-tolyl disilazane, etc. The same effect is produced by hexa-alkylcyclotrisilazanes or octaalkylcyclotetrasilazanes.

other suitable silylating agents are silylamides and silylureides such as a trialkylsilylacetamide and a bis-tri-alkylsilylacetamide. Trimethyl silyl chloride and dimethyl silyl dichloride are preferred because of their commercial availability and lower cost.

The reaction of the imine of formula II with the active acylating compounds of formula III results in far better yields of β-lactams containing a free carboxylic acid than is possible with other methods.

The stereochemistry of the final β-lactams can be controlled to obtain the major product in the cis or trans isomeric form. For instance, under certain conditions, only the trans isomer is formed and under other conditions only the cis isomer is produced.

Another feature of the invention is a novel process for the preparation of the imines of formula II having a free carboxylic group comprising reacting a free amino acid of the formula:

V wherein A' has the same meaning as A provided A contains a free carboxylic group with a silylating agent of the formula IV to convert the carboxylic group and any optionally present free acidic hydroxy group into the corresponding silyl derivative, and thereupon reacting the product obtained with an aldehyde or ketone of the formula

VI wherein X and B are as hereinbefore defined to form the silylated derivative of the imine of formula II.

The process produces the Schiff base or imino compound in essentially pure form in high yields, usually greater than 90%. If the amino acid is not reacted with a silylating agent, the reaction of the amino acid and the aldehyde or ketone results in either low yields or in a product of very low purity or in a product which cannot be isolated easily. Another advantage of this process for the preparation of the imines of formula II is that it is possible to prepare novel imines having a free acidic hydroxy group especially a hydroxy group present as a substituent in an aryl group, since such phenolic hydroxy group is protected by silylation thereof at the same time the carboxylic group is silylated.

Many of the β-lactams described here have anti-bacterial activity as determined by standards tests. Of the compounds of the invention tested 1-p-carboxyphenyl-3-phenoxy-4-α-furyl-azetidin-2-one, 1-p-methoxyphenyl-3-phenoxy-4-p-carboxy-phenyl-azetidin-2-one and 1-p-carboxyphenyl-3-phenoxy-4-p-methoxyphenyl-azetidin-2-one are outstanding for their antibacterial activity. The novel β-lactams of the invention are also useful intermediates for the preparation of complex substituted amino acids which can then be polymerized to form polymers. The amino acids are formed by 1,2-cleavage of the β-lactams with an alkali metal hydroxide or alkoxide such as sodium methoxide in a lower alkanol such as methanol to form the corresponding alkali metal salt of the resulting 3-aminopropionic acid which can be acidified to form the corresponding free amino acid.

In the following examples there are described several preferred embodiments to illustrate the invention. However, it should be understood that the invention is not intended to be limited to the specific embodiments.

EXAMPLE I 27.4 g (0.20 mole) of p-amino-benzoic acid were suspended in 100 ml of anhydrous benzene and 20.2 g (0.20 mole) of triethylamine and 22.0 g (0.20 mole) of trimethyl silyl chloride were added thereto under anhydrous conditions and the resulting mixture was stirred at room temperature for 30 minutes under completely anhydrous conditions. A solution of 24.2 g (0.20 mole) of salicylaldehyde in 50 ml of benzene was added dropwise to the mixture with constant stirring and the mixture was heated for 5 minutes to insure complete reaction. An equal volume of methylene chloride was added to the reaction mixture which was stirred for a short time to dissolve all the solid triethylamine hydrochloride and the mixture was vacuum filtered to recover the solid precipitate. The solid was crystallized from methanol to obtain 44.2 g of 2-hydroxybenzylidene-4'-carboxy-aniline melting at 269°–270° C in the form of a yellow solid. The analytical and spectral data confirmed the structure of the compound to be

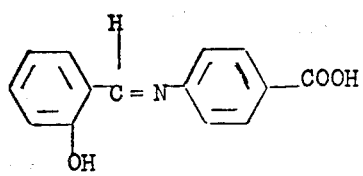

EXAMPLE II

Using the procedure of Example I, 13.7 g (0.1 mole) of anthranilic acid, 10.2 g (0.1 mole) of triethylamine and 11.0 g (0.1 mole) of trimethylsilyl chloride were reacted to form the corresponding trimethylsilyl ester which was then reacted with 13.6 g (0.1 mole) of m-anisaldehyde to obtain 18.5 g (76% yield) of 3-methoxybenzylidene-2'-carboxyaniline melting at 123°–125° C. The IR, NMR and mass spectra was consistent with the following structure:

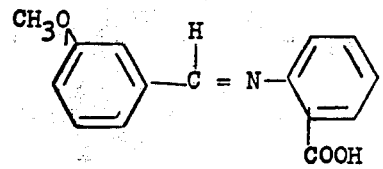

EXAMPLE III

Using the procedure of Example I, 13.7 g (0.1 mole) of p-amino-benzoic acid, 10.1 g (0.1 mole) of triethylamine and 13.7 g (0.1 mole) of trimethylsilyl chloride were reacted in anhydrous benzene to obtain the corresponding trimethylsilyl ester which was then reacted with 13.7 g (0.1 mole) of p-anisaldehyde to obtain a solid which after crystallization from methanol gave almost quantitative yields of pure 4-methoxybenzylidene-4'-carboxyaniline melting at 200°C. The analytical and spectroscopic data confirmed the following structural formula:

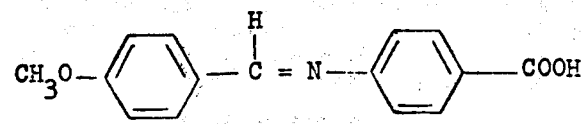

EXAMPLE IV

Equimolar proportions of 4-carboxy benzaldehyde and p-anisidene in solution in benzene were refluxed for 10 hours. A small amount of p-toluene sulfonic acid was used as catalyst and a water trap was used to take the reaction to completion. The organic solvent was evaporated off and the residue was crystallized from methanol to obtain 4-carboxybenzylidene -4'-methoxyaniline as shiny yellow needles melting at 225° C. Elemental and spectral analyses confirmed the structure to be

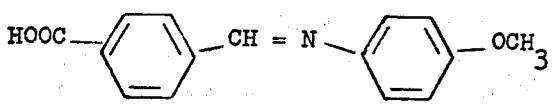

5.1 g (0.02 moles) of 4-carboxybenzylidene-4'-methoxyaniline were suspended in 100 ml of methylene chloride and 6 g (0.06 mole) of triethylamine were added thereto followed by the dropwise addition of 2.4 g (0.022 mole) of trimethylsilyl chloride. The reaction mixture was stirred at room temperature for 30 minutes under anhydrous conditions and then a mixture of 2.4 g (0.022 mole) of methoxyacetyl chloride in 100 ml of methylene chloride was added thereto over a period of 1 hour. The mixture was then heated at 40° C for 2 hours and stirred overnight at room temperature. The resulting solution was diluted with 50 ml of methylene chloride containing 5 ml of methanol and the organic solvents were distilled off under reduced pressure. The residue was thoroughly extracted with anhydrous ether and the white residue was crystallized from chloroform to obtain 6.3 g (92% yield) of the cis 3-lactam, 1-(p-methoxyphenyl)-3-methoxy-4-(p-carboxyphenyl) - azetidin-2-one melting at 233°C having the structural formula:

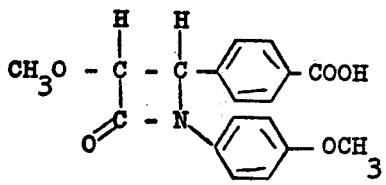

NMR (Dimethylsulfoxide - $d_6$). Peaks: $\tau$, 2.87 (broad, 1H); 1.9 – 3.2 (8H); 4.48 (d, 1H, J = 5 cps, cis); 4.99 (d, 1H, J = 5 cps, cis); 6.31 (S, 3H); 6.92 (S, 3H). Mass. spec., $M^+$, m/e. 327.

EXAMPLE V

Using the procedure of Example IV, 4-carboxybenzylidene-4'-methoxyaniline and α-phenoxyacetyl chloride were reacted in equimolar amounts to obtain the cis β-lactam, 1-(p-methoxyphenyl)-3-phenoxy-4-(p-carboxyphenyl)-azetidin-2-one melting at 246°C.

EXAMPLE VI

Using the procedure of Example IV, 4-carboxybenzylidene-4'-methoxyaniline was reacted with an equimolar amount of α-azido-acetyl chloride to obtain 1-(p-methoxyphenyl)-3-azido-4(p-carboxyphenyl)-azetidin-2-one melting at 190°C.

EXAMPLE VII

Using the procedure of Example IV, 4-carboxybenzylidene-4'-methoxyaniline was reacted with an equimolar amount of phthalimidoacetyl chloride to obtain 1-(p-methoxyphenyl)-3-phthalimido-4-(p-carboxyphenyl)-azetidin-2-one melting at 265°C.

EXAMPLE VIII

Using the procedure of Example IV, 4-methoxy-benzylidene-4'-carboxyaniline was reacted with an equimolar amount of methoxyacetyl chloride to obtain 1-(p-carboxyphenyl)-3-methoxy-4-(p-methoxyphenyl)-azetidin-2-one and was a 70–30 mixture of cis and trans isomers.

EXAMPLE IX

Using the procedure of Example IV, 4-methoxybenzylidene-4'-carboxyaniline was reacted with an equimolar amount of phenoxyacetyl chloride to obtain 1-(p-carboxyphenyl)-3-phenoxy-4-(p-methoxyphenyl)-azetidin-2-one melting at 268°C.

EXAMPLE X

Using the procedure of Example IV, except that double the usual amount of silylating agent was used, 2-hydroxybenzylidene-4'-carboxyaniline was reacted with an equimolar amount of phenoxyacetyl chloride to obtain cis-1-(p-carboxyphenyl)-3-phenoxy-4-(o-hydroxyphenyl)azetidin-2-one melting at 219°C. The product occurred as a 50–50 mixture of the cis and trans isomers but the cis-product can be easily separated because of its low solubility in various organic solvents.

EXAMPLE XI

Using the procedure of Example IV, 4-dimethylaminobenzylidene-4'-carboxyaniline (made by method of Example I - m.p. 265°–267°C) was reacted with an equimolar amount of phenoxyacetyl chloride to obtain 1-(p-carboxy-phenyl)-3-phenoxy-4-(p-dimethylaminophenyl)-azetidin-2-one melting above 300°C. The said compound was a mixture of 40% cis and 60% trans isomers.

EXAMPLE XII

Using the procedure of Example IV, azidoacetyl chloride and 4-methoxybenzylidene-4'-carboxyaniline were reacted to obtain the trans β-lactam, 1-(p-carboxyphenyl)-3-azido-4-(p-methoxyphenyl)-azetidin-2-one melting at 127°–129°C.

EXAMPLE XIII

Using the procedure of Example IV, equimolar amounts of 4-carboxybenzylidene-4'-veratrylamine[-prepared by method of Example IV-m.p-150°–151°C] and phenoxyacetyl chloride were reacted to obtain the cis β-lactam, 1-veratryl-3-phenoxy-4-(p-carboxyphenyl)-azetidin-2-one melting at 160°–161°C.

EXAMPLE XIV

Using the procedure of Example IV, azidoacetyl chloride and 4-nitro-benzylidene-4'-carboxyaniline were reacted to yield 1-(p-carboxyphenyl)-3-azido-4-(p-nitrophenyl)-azetidin-2-one. It was a mixture of 67% cis and 33% trans isomers as shown by its NMR spectrum.

EXAMPLE XV

Using the procedure of Example-IV, 4-nitrobenzylidene-4'-carboxyaniline[prepared by the method of Example I-m.p.-256°–260°C] and phenoxyacetyl chloride were reacted to obtain 1-(p-carboxyphenyl)-3-phenoxy-4-(p-nitrophenyl)-azetidin -2-one. The said compound was a mixture of 60% cis and 40% trans isomers.

EXAMPLE XVI

A mixture of 2g of 1-veratryl-3-phenoxy-4-p-carboxyphenyl-azetidin-2-one and 800 mg of potassium hydroxide dissolved in 10 ml of water and diluted with 100 ml of methanol was refluxed for 10 hrs. on a steam bath. Removal of the solvent provided a white residue which was dissolved in water and filtered to remove any unreacted material. Acidification of the clear solution provided a white solid which was collected by vacuum filtration and crystallized from $CHCl_3$ to obtain a 70% yield of 2-p-carboxy phenyl-2-veratrylamino-1-phenoxy-propionic acid melting at 238°–239°C. The IR and MNR analyses confirmed its structure to be:

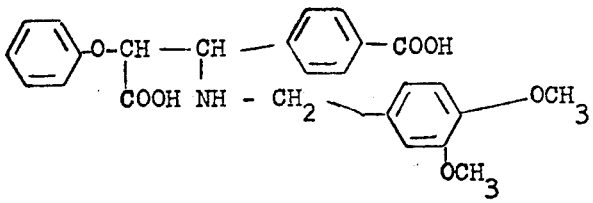

Moreover, 1-p-carboxyphenyl-3-phenoxy-4-furyl-azetidin-2-one has been prepared by the process of the invention.

ANTIBACTERIAL ACTIVITY

A stock solution of the test compounds at a concentration of 2000 mg/cc in 0.05 molar phosphate buffer solution at a pH of 6.5 was prepared and two-fold dilutions were made with sterile buffer. 1 cc quantities of each dilution were then incorporated into 19 cc of brain heart infusion agar in sterile petri dishes. The hardened surface was then inoculated with the test organisms and it was then incubated for 18 hours at 37°C. The minimum inhibitory concentration (MIC) which is the least amount of compound completely inhibiting the test organism is determined in mg/cc. The results are given in Table II.

TABLE II

| Compound | Organism | MIC M/c in mg/cc |
|---|---|---|
| 1-p-carboxyphenyl-3-phenoxy-4-furyl azetidin-2-one | Bacillius Subtilis ATCC 6633 | 50 |
|  | Staphylococcus Aureus A 55 | 50 |
| 1-p-methoxyphenyl-3-phenoxy-4-p-carboxy-phenyl-azetidin-2-one | Bacillus subtilis ATCC6633 | 100 |
|  | Staphylococcus Aureus A 55 | 100 |
|  | Staphylococcus Aureus A 321 | 100 |
|  | Staphylococcus Aureus A 355 | 100 |
|  | Staphylococcus Aureus 2160' | 100 |
| 1-p-carboxyphenyl-3-phenoxy-4-p-methoxy-phenyl-azetidin-2-one | Staphylococcus Aureus A 55 | 50 |

Various modifications of the compositions and processes of the invention may be made without departing from the spirit or scope thereof and it should be understood that the invention is intended to be limited only as defined in the appended claims.

I claim:

1. A β-lactam of the formula

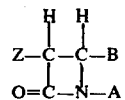

wherein A and B are each selected from the group consisting of phenyl, phenyl lower alkyl of 1 to 7 alkyl carbon atoms and furyl with A or B being substituted with a carboxyl and the other group being optionally substituted with a member of the goup consisting of hydroxy, 1 to 2 lower alkoxy, nitro and diloweralkylamino, and Z is selected from the group consisting of lower alkoxy, phenoxy, phthalimido and —$N_3$.

2. A compound of claim 1 wherein Z is selected from the group consisting of methoxy, phenoxy, phthalimido and —$N_3$, and A and B are selected from the group consisting of phenyl, benzyl and furyl with A or B being substituted with a carboxyl and the other being optionally substituted with hydroxy, nitro, dimethylamine or 1 or 2 methoxy.

3. A compound of claim 1 which is 1-(p-methoxyphenyl)-3-methoxy-4-(p-carboxyphenyl)-azetidin-2-one.

4. A compound of claim 1 which is 1-(p-carboxyphenyl) -3-azido-4-(p-nitrophenyl)-azetidin-2-one.

5. A compound of claim 1 which is 1-veratryl-3-phenoxy-4-(p-carboxyphenyl)-azetidin-2-one.

6. A compound of claim 1 which is 1-p-carboxyphenyl-3-phenoxy-4-furyl-azetidin-2-one.

7. A compound of claim 1 which is 1-p-carboxyphenyl-3-phenoxy-4-p-methoxyphenyl-azetidin-2-one.

8. A compound of claim 1 which is 1-p-methoxyphenyl-3-phenoxy-4-p-carboxyphenyl-azetidin-2-one.

* * * * *